US012616826B2

(12) United States Patent
Sharma et al.

(10) Patent No.: US 12,616,826 B2
(45) Date of Patent: May 5, 2026

(54) PUSH-PULL TIGHTENING PORT FOR PERCUTANEOUS CIRCULATORY SUPPORT DEVICE REPOSITIONING AND AXIAL LOCKING, AND ATTACHMENT TO SHEATH HUB

(71) Applicants: Boston Scientific Medical Device Limited, Galway (IE); Boston Scientific Scimed Inc., Maple Grove, MN (US)

(72) Inventors: Neeraj Kumar Sharma, New Delhi (IN); Sumit Agrawal, Haryana (IN); Rupesh Kumar Pahwa, Gurugram (IN); Qian Liu, Plymouth, MN (US)

(73) Assignees: Boston Scientific Medical Device Limited, Galway (IE); Boston Scientific Scimed, Inc., Maple Grove, MN (US)

( * ) Notice: Subject to any disclaimer, the term of this patent is extended or adjusted under 35 U.S.C. 154(b) by 435 days.

(21) Appl. No.: 18/116,634

(22) Filed: Mar. 2, 2023

(65) Prior Publication Data

US 2023/0277834 A1     Sep. 7, 2023

Related U.S. Application Data

(60) Provisional application No. 63/316,221, filed on Mar. 3, 2022.

(51) Int. Cl.
 A61M 39/06 (2006.01)
 A61M 60/13 (2021.01)
 (Continued)

(52) U.S. Cl.
 CPC ........ *A61M 39/0606* (2013.01); *A61M 60/13* (2021.01); *A61M 60/216* (2021.01); *A61M 60/865* (2021.01); *A61M 2039/0258* (2013.01)

(58) Field of Classification Search
 CPC .................................................. A61M 39/0613
 See application file for complete search history.

(56) References Cited

U.S. PATENT DOCUMENTS 4,886,507 A   12/1989  Patton et al.
5,254,097 A   10/1993  Schock et al.
          (Continued)

FOREIGN PATENT DOCUMENTS

EP        3866876 B1    11/2022
KR      102295750 B1     9/2021
          (Continued)

OTHER PUBLICATIONS

International Search Report and Written Opinion for International Application No. PCT/US2023/014364, dated May 30, 2023. (19 pages).

*Primary Examiner* — George R Evanisko
(74) *Attorney, Agent, or Firm* — Seager, Tufte & Wickhem LLP

(57)     ABSTRACT

A tightening port for use with a hemostasis valve of an introducer sheath includes a gripper configured for engagement with the hemostasis valve hub, the gripper having a proximal end, a distal end, a cylindrical body defining a lumen, and a plurality of protrusions extending from the proximal end, a base having a cylindrical body and a lumen defined therethrough for receiving a portion of the gripper, and a plurality of engagement features configured for engaging with the plurality of protrusions of the gripper, and wherein the lumen of the gripper has an initial diameter prior to engagement with the base, and the lumen of the gripper has a compressed diameter after engagement with the base, wherein the compressed diameter is less than the initial diameter.

13 Claims, 9 Drawing Sheets

(51) Int. Cl.
  *A61M 60/216*  (2021.01)
  *A61M 60/865*  (2021.01)
  *A61M 39/02*  (2006.01)

(56)  References Cited

U.S. PATENT DOCUMENTS

| | | | |
|---|---|---|---|
| 5,295,969 A | 3/1994 | Fischell et al. |
| 5,324,271 A | 6/1994 | Abiuso et al. |
| 5,935,112 A | 8/1999 | Stevens et al. |
| 6,692,462 B2 | 2/2004 | Mackenzie et al. |
| 7,027,875 B2 | 4/2006 | Siess et al. |
| 8,888,728 B2 | 11/2014 | Aboul-Hosn et al. |
| 9,937,319 B1 | 4/2018 | Leeflang et al. |
| 10,709,828 B2 | 7/2020 | Toellner et al. |
| 10,737,008 B2 | 8/2020 | Corbett et al. |
| 11,833,314 B2 | 12/2023 | Corbett et al. |
| 2003/0088213 A1 | 5/2003 | Schweikert et al. |
| 2005/0197624 A1 | 9/2005 | Goodson et al. |
| 2006/0047266 A1 | 3/2006 | Elkins et al. |
| 2008/0033396 A1 | 2/2008 | Danek et al. |
| 2008/0183163 A1 | 7/2008 | Lampropoulos et al. |
| 2008/0188831 A1 | 8/2008 | Bonnette et al. |
| 2009/0259200 A1 | 10/2009 | Lampropoulos et al. |
| 2010/0036329 A1 | 2/2010 | Razack |
| 2010/0100044 A1 | 4/2010 | Ye et al. |
| 2011/0004223 A1 | 1/2011 | Leeflang et al. |
| 2011/0077621 A1 | 3/2011 | Graham et al. |
| 2014/0025037 A1 | 1/2014 | Elkins et al. |
| 2015/0141738 A1 | 5/2015 | Toellner et al. |
| 2016/0166821 A1* | 6/2016 | Weiss ................ A61M 39/0613 |
| | | | 604/164.02 |
| 2017/0049947 A1 | 2/2017 | Corbett et al. |
| 2018/0326197 A1* | 11/2018 | McArthur ....... A61M 25/09041 |
| 2019/0167967 A1 | 6/2019 | Mottola et al. |
| 2020/0121905 A1 | 4/2020 | Zoll |
| 2020/0289794 A1 | 9/2020 | Fantuzzi |
| 2020/0391014 A1 | 12/2020 | Walters et al. |
| 2021/0085923 A1 | 3/2021 | Fantuzzi et al. |
| 2021/0170081 A1 | 6/2021 | Kanz |
| 2021/0260361 A1 | 8/2021 | Charafeddine et al. |
| 2023/0270988 A1 | 8/2023 | Sharma et al. |

FOREIGN PATENT DOCUMENTS

| | | |
|---|---|---|
| WO | 9813083 A1 | 4/1998 |
| WO | 2016001439 A1 | 1/2016 |
| WO | 2019032520 A2 | 2/2019 |

* cited by examiner

300

Inserting an Introducer Sheath into a Blood Vessel — 302

Inserting a Medical Device Through a Proximal End of the Valve Hub — 304

Inserting a Gripper over the Medical Device and Engaging the Gripper with the Valve Hub — 306

Engaging a Base of a Tightening Port with the Gripper to Axially Secure the Medical Device — 308

PUSH-PULL TIGHTENING PORT FOR PERCUTANEOUS CIRCULATORY SUPPORT DEVICE REPOSITIONING AND AXIAL LOCKING, AND ATTACHMENT TO SHEATH HUB

CROSS-REFERENCE TO RELATED APPLICATION

This application claims priority to U.S. Provisional Application No. 63/316,221, filed Mar. 3, 2022, which is herein incorporated by reference in its entirety.

TECHNICAL FIELD

The present disclosure relates to a locking attachment to a hub of an introducer sheath. More specifically, the present disclosure relates to a push-pull tightening port attachment that allows for repositioning and axial locking of a medical device positioned within a hub of the introducer sheath.

BACKGROUND

In various procedures for delivering intravascular medical devices, an introducer sheath is inserted into a blood vessel of a patient, for example a femoral artery, and medical devices are inserted into the introducer sheath for introduction into the blood vessel. In various instances, the medical devices include catheters or other medical devices such as a blood pump. A hub, for example a hemostasis valve hub, may be incorporated at a proximal end of the introducer sheath to reduce blood leakage as devices are being inserted, positioned, and removed. In various instances, there may be a desire for repositioning of the medical device and stabilization of the medical device upon repositioning. There is a need for increased axial stabilization of the medical devices inserted into the hemostasis valve hub and the introducer sheath while still facilitating passage of the devices through the introducer sheath and allowing for repositioning of the devices.

SUMMARY

In Example 1, a tightening port for use with a hub of a sheath includes a gripper configured for engagement with the hub of the sheath, the gripper having a proximal end, a distal end, a cylindrical body defining a lumen, and a plurality of protrusions extending from the proximal end, a base having a cylindrical body and a lumen defined therethrough for receiving a portion of the gripper, and a plurality of engagement features configured for engaging with the plurality of protrusions of the gripper, and wherein the lumen of the gripper has an initial diameter prior to engagement with the base, and the lumen of the gripper has a compressed diameter after engagement with the base, wherein the compressed diameter is less than the initial diameter.

In Example 2, the tightening port of Example 1 further includes wherein the hub includes a hemostasis valve hub and the gripper comprises a plurality of posts configured for engaging with the hub.

In Example 3, the tightening port of Example 1 or Example 2 further includes wherein the plurality of protrusions of the gripper includes at least four protrusions extending from the cylindrical body.

In Example 4, the tightening port of Example 3 further includes wherein each of the protrusions of the gripper has a block extending radially outward form the protrusion.

In Example 5, the tightening port of any one of Examples 1-4 further includes wherein the base has an outer surface with a plurality of ribs extending circumferentially around the outer surface.

In Example 6, the tightening port of any one of Examples 1-5 further includes wherein the plurality of engagement features comprises at least four protrusions that extend radially inward from an outer circumference of the base.

In Example 7, the tightening port of Example 6 further includes wherein each of the protrusions includes a detent configured for receiving a portion of the protrusions of the gripper for engagement with the gripper.

In Example 8, the tightening port of any one of Examples 1-7 further includes wherein the base includes an extension configured for receiving a sleeve holder.

In Example 9, delivery system for introducing at least one medical device into a blood vessel includes a sheath configured for insertion into the blood vessel, the sheath having a proximal end and a distal end, a valve hub having a proximal end and a distal end and the distal end configured for attachment with the proximal end of the sheath, and a tightening port configured for attachment with the proximal end of the valve hub. The tightening port includes a gripper configured for engagement with the hemostasis valve, the gripper having a proximal end, a distal end, a cylindrical body defining a lumen, and a plurality of protrusions extending from the proximal end, a base having a cylindrical body and a lumen defined therethrough for receiving a portion of the gripper, and a plurality of engagement features configured for engaging with the plurality of protrusions of the gripper, wherein the lumen of the gripper has an initial diameter prior to engagement with the base, and the lumen of the gripper has a compressed diameter after engagement with the base, wherein the compressed diameter is less than the initial diameter.

In Example 10, the delivery system of Example 9 further includes wherein the tightening port further includes a sleeve holder engaged with an extension of the base.

In Example 11, the delivery system of Example 9 or Example 10 further includes wherein the plurality of engagement features of the base include a plurality of protrusions extending radially inwardly from an outer circumference of the base.

In Example 12, the delivery system of Example 11 further includes wherein each of the plurality of engagement features includes a detent for receiving a portion of the each of the plurality of protrusions of the gripper.

In Example 13, a method for delivering at least one medical device into a blood vessel includes inserting a sheath into the blood vessel, the sheath having the proximal end and a distal end and a valve hub positioned on the proximal end, inserting a medical device through the proximal end of the valve hub, inserting a gripper of a tightening port over the medical device and engaging the gripper with the proximal end of the valve hub, and engaging a base of a tightening port with the gripper, such that the base is positioned over the catheter to axially secure the medical device.

In Example 14, the method of Example 13 further includes wherein the gripper includes a plurality of protrusions extending from a proximal end of the gripper.

In Example 15, the method of Example 13 or Example 14 further includes wherein engaging the base of the tightening port tightens the positioning of the gripper around the medical device to secure the axial positioning of the medical device within the valve hub.

In Example 16, a tightening port for use with a hemostasis valve of an sheath includes a gripper configured for engagement with the hemostasis valve hub, the gripper having a proximal end, a distal end, a cylindrical body defining a lumen, and a plurality of protrusions extending from the proximal end, a base having a cylindrical body and a lumen defined therethrough for receiving a portion of the gripper, and a plurality of engagement features configured for engaging with the plurality of protrusions of the gripper, and wherein the lumen of the gripper has an initial diameter prior to engagement with the base, and the lumen of the gripper has a compressed diameter after engagement with the base, wherein the compressed diameter is less than the initial diameter.

In Example 17, the tightening port of Example 16 further includes wherein the gripper includes a plurality of posts configured for engaging with the hemostasis valve hub.

In Example 18, the tightening port of Example 16 further includes wherein the plurality of protrusions of the gripper comprises at least four protrusions extending from the cylindrical body.

In Example 19, the tightening port of Example 18 further includes wherein each of the protrusions of the gripper has a block extending radially outward form the protrusion.

In Example 20, the tightening port of Example 16 further includes wherein the base has an outer surface with a plurality of ribs extending circumferentially around the outer surface.

In Example 21, the tightening port of Example 16 further includes wherein the plurality of engagement features comprises at least four protrusions that extend radially inward from an outer circumference of the base.

In Example 22, the tightening port of Example 21 further includes wherein each of the protrusions comprises a detent configured for receiving a portion of the protrusions of the gripper for engagement with the gripper.

In Example 23, the tightening port of Example 16 further includes wherein the initial diameter has a value of approximately 3.3 mm.

In Example 24, the tightening port of Example 16 further includes wherein the compressed diameter has a value of approximately 2.8 mm.

In Example 25, the tightening port of Example 16 further includes wherein the base comprises an extension configured for receiving a sleeve holder.

In Example 26, a delivery system for introducing at least one medical device into a blood vessel includes a sheath configured for insertion into the blood vessel, the sheath having a proximal end and a distal end, a valve hub having a proximal end and a distal end and the distal end configured for attachment with the proximal end of the sheath, and a tightening port configured for attachment with the proximal end of the valve hub. The tightening port includes a gripper configured for engagement with the hemostasis valve, the gripper having a proximal end, a distal end, a cylindrical body defining a lumen, and a plurality of protrusions extending from the proximal end, a base having a cylindrical body and a lumen defined therethrough for receiving a portion of the gripper, and a plurality of engagement features configured for engaging with the plurality of protrusions of the gripper, wherein the lumen of the gripper has an initial diameter prior to engagement with the base, and the lumen of the gripper has a compressed diameter after engagement with the base, wherein the compressed diameter is less than the initial diameter.

In Example 27, the delivery system of Example 26 further includes wherein the tightening port further includes a sleeve holder engaged with an extension of the base.

In Example 28, the delivery system of Example 26 further includes wherein the plurality of engagement features of the base include a plurality of protrusions extending radially inwardly from an outer circumference of the base.

In Example 29, the delivery system of Example 28 further includes wherein each of the plurality of engagement features includes a detent for receiving a portion of the each of the plurality of protrusions of the gripper.

In Example 30, the delivery system of Example 29 further includes wherein each of the plurality of protrusions includes a block extending radially outward from the protrusion and is received within each of the detents of the base.

In Example 31, a method for delivering at least one medical device into a blood vessel includes inserting a sheath into the blood vessel, the sheath having the proximal end and a distal end and a valve hub positioned on the proximal end, inserting a medical device through the proximal end of the valve hub, inserting a gripper of a tightening port over the medical device and engaging the gripper with the proximal end of the valve hub, and engaging a base of a tightening port with the gripper, such that the base is positioned over the catheter to axially secure the medical device.

In Example 32, the method of Example 31 further includes wherein the gripper includes a plurality of protrusions extending from a proximal end of the gripper.

In Example 33, the method of Example 32 further includes wherein the base includes a plurality of engagement features extending inwardly from an outer circumference of the base, and wherein the engaging the base includes engaging the plurality of engagement features of the base with the plurality of protrusions of the gripper.

In Example 34, the method of Example 31 further includes wherein engaging the base of the tightening port tightens the positioning of the gripper around the medical device to secure the axial positioning of the medical device within the valve hub.

In Example 35, the method of Example 32 further includes wherein the method further includes engaging a sleeve holder with a distal end of the base.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
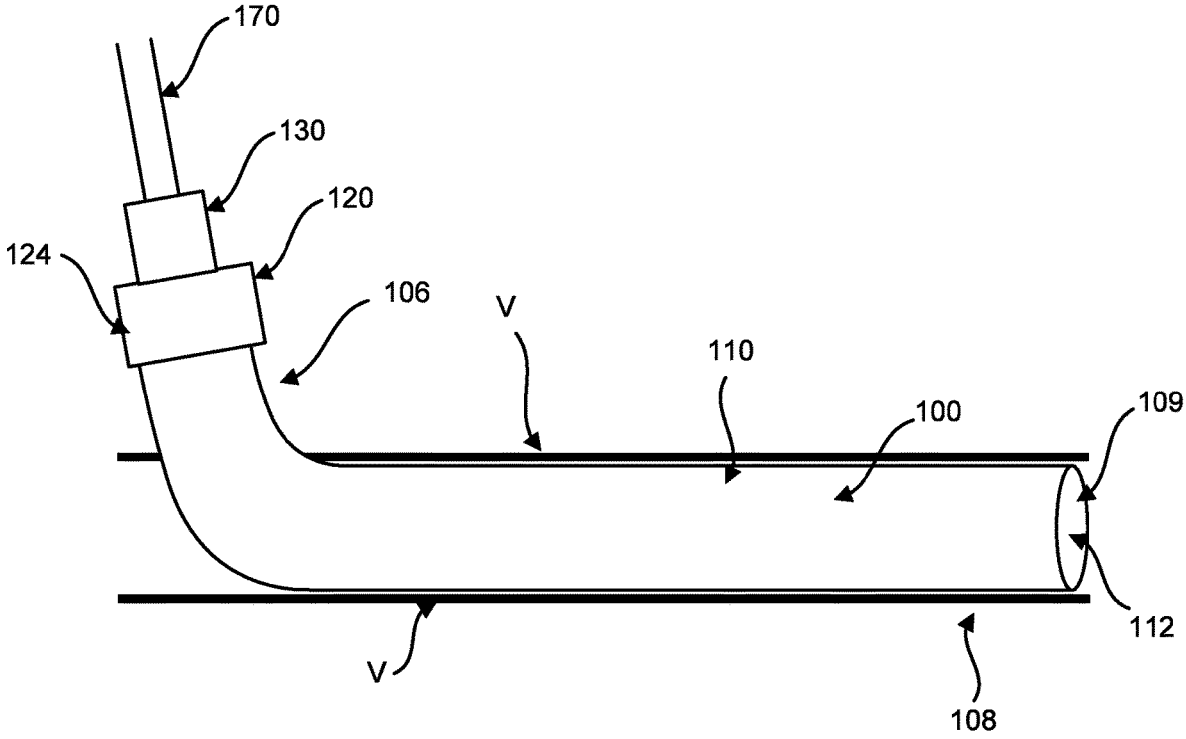
FIG. 1 illustrates a cross sectional view of an introducer sheath extending to an introducer sheath, in accordance with embodiments of the present disclosure.
Figure 2:
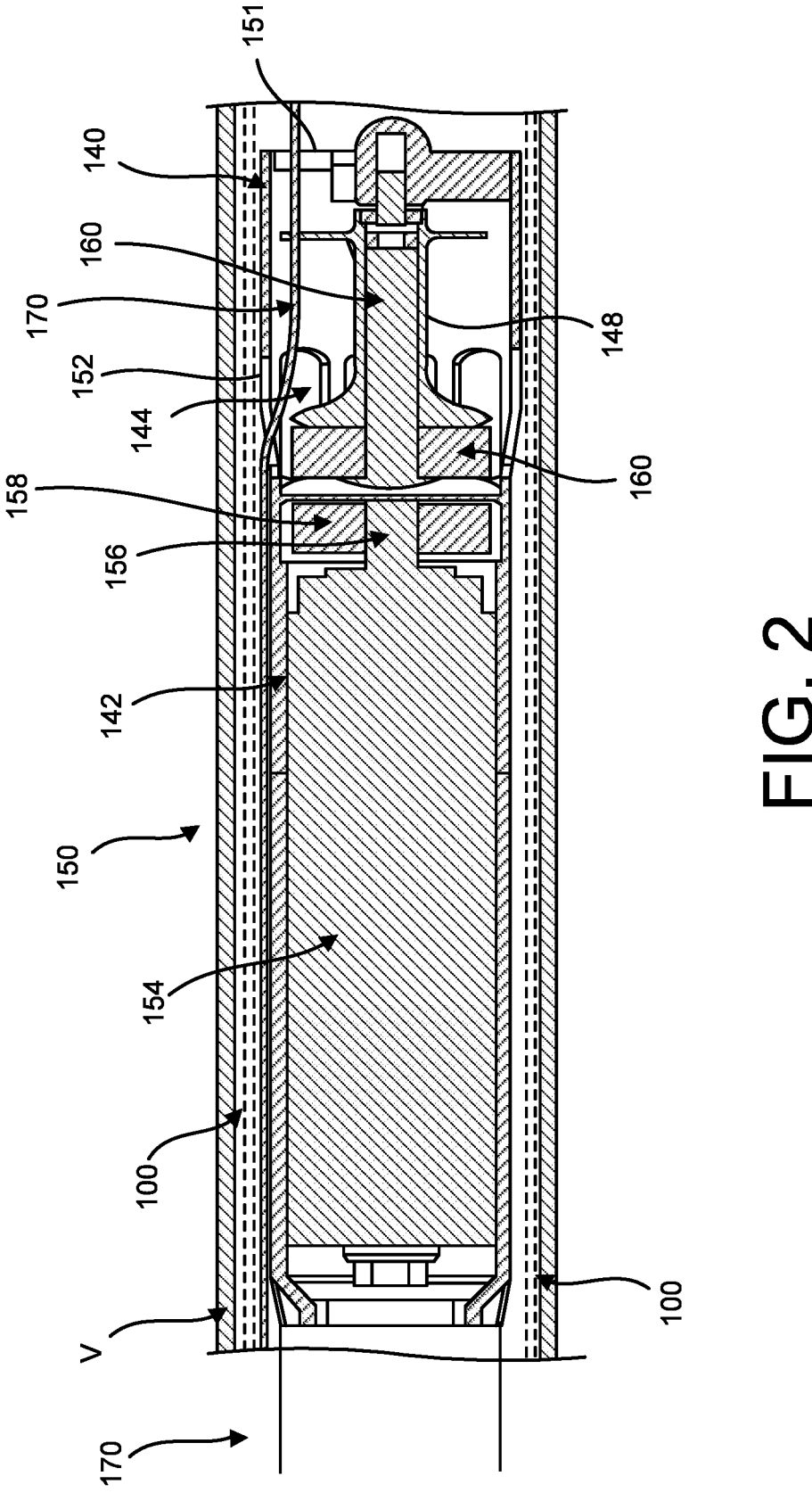
FIG. 2 illustrates a cross sectional view of a medical device positioned within a blood vessel, in accordance with embodiments of the present disclosure.

FIG. 1 illustrates a side cross sectional view of a blood vessel V with a sheath 100, such as an introducer sheath 100, inserted at least partially into the blood vessel V. In some embodiments, the introducer sheath 100 is used for facilitating the passage of various relatively large medical devices, such as a blood pump as will be described further herein, through the introducer sheath 100 and into the blood vessel V. Hence, the introducer sheath 100 may be referred to as a large bore introducer sheath. The introducer sheath 100 comprises a proximal end 106 and a distal end 108 that is opposite the proximal end 106. The introducer sheath 100 includes a proximal opening (not shown) adjacent the proximal end 106 and a distal opening 109 adjacent the distal end 108. A body portion 110 of the introducer sheath 100 extends between the proximal end 106 and the distal end 108, and the body portion 110 defines a lumen 112 of the introducer sheath 100. The introducer sheath 100 may be formed by various polymeric or metallic materials. In further embodiments, the introducer sheath 100 may comprise an additional surface coating. The surface coating may include, but is not limited to, silicone, PET, or any other applicable polymer. A hub 120 is commonly included at the proximal opening 107. The hub 120, also referred to herein as a hemostasis valve hub, is configured for hemostasis, i.e., to prevent blood from leaking out of the introducer sheath 100 during use. While described herein as a hemostasis valve hub, a different embodiment of a hub may be incorporated. A medical device, for example a catheter 170, may be inserted through the hub 120 and the introducer sheath 100 and the hub 120 may maintain hemostasis between the catheter 170, the introducer sheath 100 and the external surroundings. In some embodiments, the catheter 170 may couple to a distally extending medical device, such as the blood pump 150 as shown in FIG. 2. After insertion of the catheter 170, it may be desired for axial stabilization of the catheter 170 to ensure that it (and any coupled medical device) does not shift axial positioning during use. Further, in these instances, it may also be desired for the operator to reposition the catheter 170 (and any coupled medical device) after insertion in order to place it in the desired positioning throughout operation. As such, a tightening port 130 may be positioned on a proximal end 124 of the hub 120 to provide for axial securement or stabilization of the catheter 170. The tightening port 130 may also provide the ability for easier repositioning and stabilization of the catheter 170, as will be described further herein.

In some embodiments, the sheath 100 may be a repositioning sheath.

FIG. 2 illustrates a cross-sectional view of the introducer sheath 100 of FIG. 1 after insertion of a medical device, illustratively a blood pump 150, into the introducer sheath 100. As noted above, in some embodiments a catheter, such as the catheter 170, may be coupled to the proximal end of the blood pump 150 and extend outside the blood vessel V. The blood pump 150 generally includes an impeller assembly housing 140 and a motor housing 142. In some embodiments, the impeller assembly housing 140 and the motor housing 142 may be integrally or monolithically constructed. The impeller assembly housing 140 carries an impeller assembly 144 therein. The impeller assembly 144 includes an impeller shaft 146 and an impeller 148 that rotates relative to the impeller assembly housing 140 to drive blood through the blood pump 150. More specifically, the impeller 148 causes blood to flow from a blood inlet 151 formed on the impeller assembly housing 140, through the impeller assembly housing 140, and out of a blood outlet 152 formed on the impeller assembly housing 140. In some embodiments, the impeller shaft 146 and the impeller 148 may be integrated, and in other embodiments the impeller shaft 146 and the impeller 148 may be separate components. As shown in FIG. 2, the inlet 151 may be formed on an end portion of the impeller assembly housing 140 and the outlet 152 may be formed on a side portion of the impeller assembly housing 140. In other embodiments, the inlet 151 and/or the outlet 152 may be formed on other portions of the impeller assembly housing 140. In some embodiments, the impeller assembly housing 140 may couple to a distally extending cannula (not shown), and the cannula may receive and deliver blood to the inlet 151.

With continued reference to FIG. 2, the motor housing 142 carries a motor 154, and the motor 154 is configured to rotatably drive the impeller 148 relative to the impeller assembly housing 140. In the illustrated embodiment, the motor 154 rotates a drive shaft 156, which is coupled to a driving magnet 158. Rotation of the driving magnet 158 causes rotation of a driven magnet 160, which is connected to the impeller assembly housing 140. More specifically, in embodiments incorporating the impeller shaft 146, the impeller shaft 146 and the impeller 148 are configured to rotate with the driven magnet 160. In other embodiments, the motor 154 may couple to the impeller assembly housing 140 via other components. Additionally, as illustrated in FIG. 2, the catheter 170 extends from a proximal end of the blood pump 150. In some embodiments, the catheter 170 may be coupled to the motor housing 142 through a tapering connector and/or various other connecting means. The catheter 170 may have a flexible construction to facilitate to the delivery of the blood pump 150. While the introducer sheath 100 is illustrated above with the use of the blood pump 150, various other medical devices may be used in conjunction with the introducer sheath 100 and the hemostasis valve hub 120. For example, another variation of a blood pump may be used in conjunction with the introduce sheath 100. In other examples, a medical device other than a blood pump may be incorporated.

Figure 3:
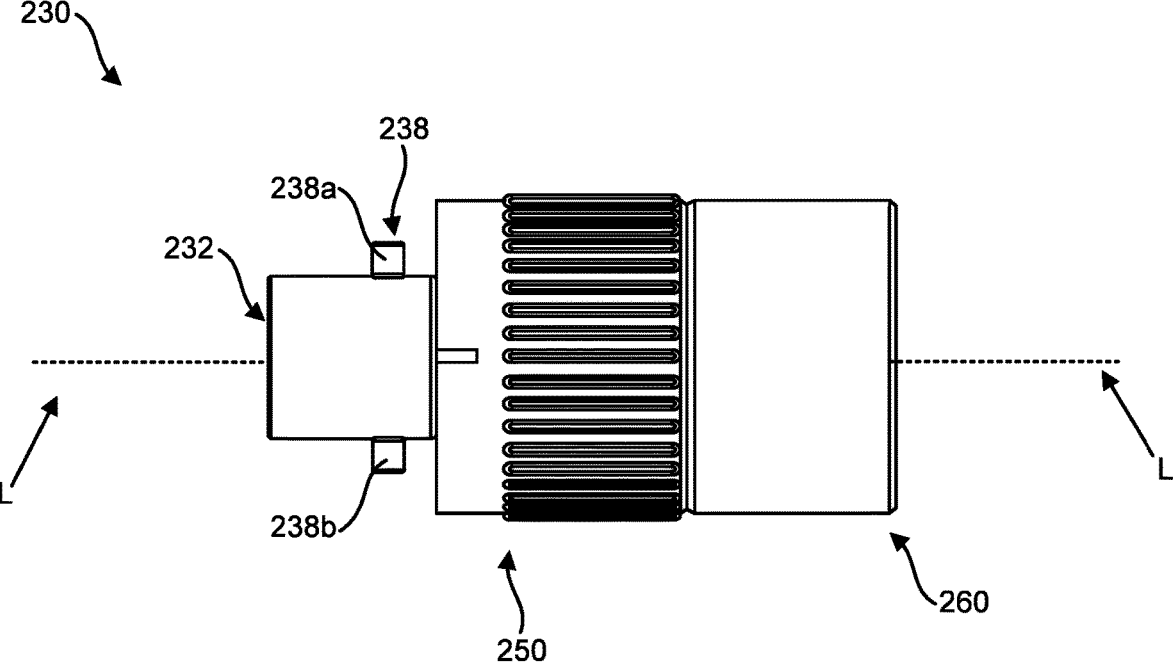
FIG. 3 illustrates a side view of a tightening port for use with an introducer sheath, in accordance with embodiments of the present disclosure.
Figure 4:
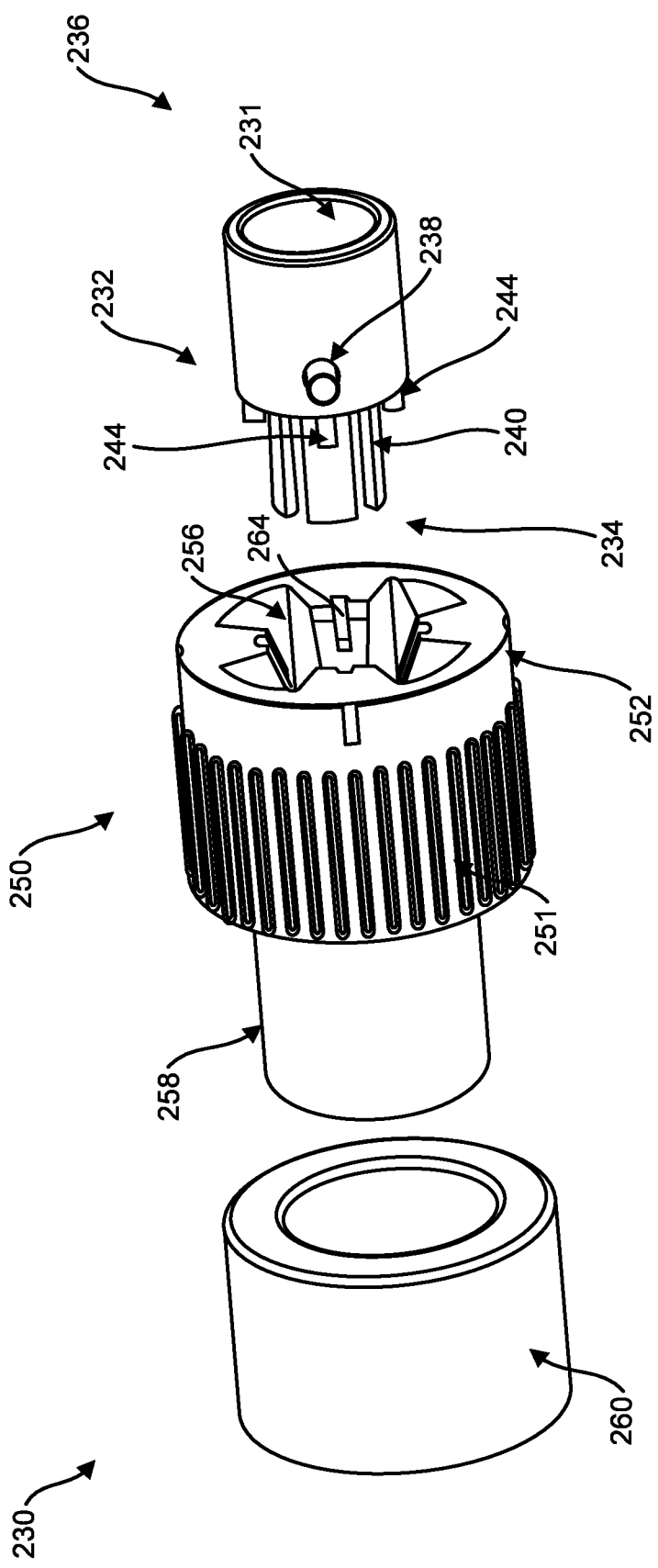
FIG. 4 illustrates an exploded view of the tightening port of FIG. 3, in accordance with embodiments of the present disclosure.

FIG. 3 and FIG. 4 illustrate an embodiment of a tightening port 230 for engaging with the proximal end 124 of the hemostasis valve hub 120. The tightening port 230 extends along a longitudinal axis L and defines a lumen (not shown), having a diameter (not shown) defined by a diameter of a gripper 232, as will be described further herein. The tightening port 230 includes the gripper 232. The gripper 232 has a generally cylindrical shape defining a lumen 231 (FIG. 4) extending through the gripper 232 and has a plurality of posts 238 extending radially outward from the gripper 232. More specifically, the gripper 232 comprises a first post 238a and a second post 238b positioned generally opposite the first post 238a. Adjacent the gripper 232 is a base 250 engaged with the gripper 232. The base 250 may have an outer surface with a plurality of ribs 251 for easier grasping by an operator to adjust the base 250, as will be described further herein. Adjacent the base 250 is an optional sleeve holder 260 configured for receiving a sterile sleeve for use by the operator during operation.

FIG. 4 illustrates an exploded view of the tightening port 230. As illustrated, the gripper 232 comprises a proximal end 234 and a distal end 236 opposite the proximal end 234. The proximal end 234 of the gripper 232 comprises a plurality of protrusions 240 extending from the proximal end 234. For example, in some embodiments, the plurality of protrusions 240 includes at least four protrusions. However, varying amounts of protrusions 240 may be incorporated. As illustrated, each of the plurality of protrusions 240 includes a block 244 extending radially outward from each of the plurality of protrusions 240. As illustrated, each block 244 may extend a length that is less than a length of each of the plurality of protrusions 240. As will be described further with reference to FIGS. 6A-6B, the plurality of protrusions 240 are configured to engage with a distal end 252 of the base 250. More specifically, and as will be described with reference to FIGS. 6A-6B, the distal end 252 of the base 250 comprises a plurality of engagement features 256 for engaging with the plurality of protrusions 240 of the gripper 232. In some embodiments, the plurality of engagement features 256 may include a plurality of protrusions extending radially inward from an outer circumference of the base 250. Further, the base 250 comprises an extension 258 that extends proximally from the base 250. The extension 258 is configured for receiving a sleeve holder 260 for positioning over a sterile sleeve to cover the medical device.

Figure 5:
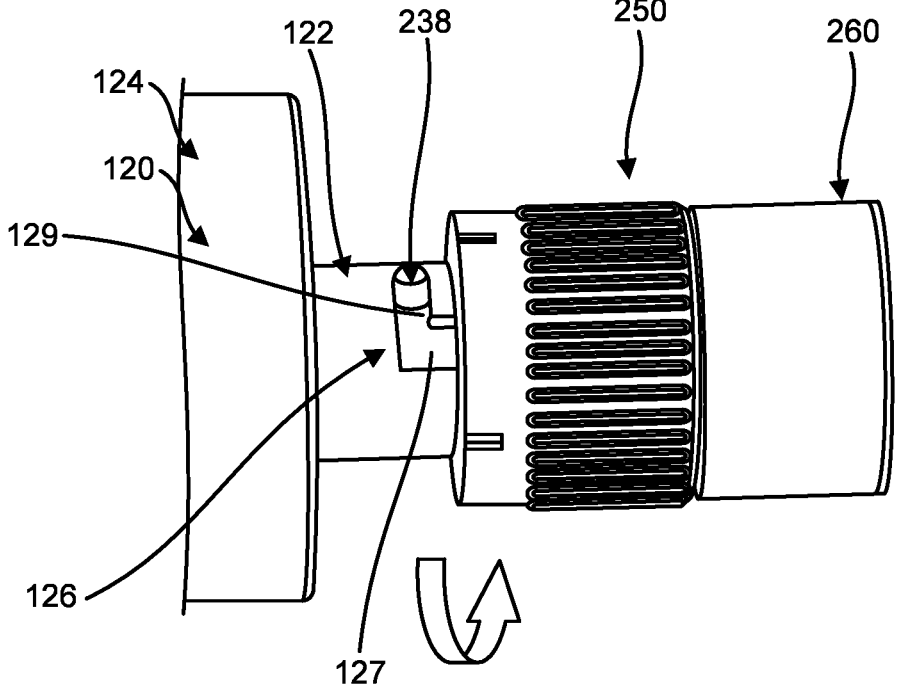
FIG. 5 illustrates a side view of a portion of the tightening port of FIG. 3, in accordance with embodiments of the present disclosure.

As previously described, the tightening port 230 is configured for engagement with the valve hub. FIG. 5 illustrates the gripper 232 engaged with the hub 120. More specifically, the hub 120 comprises an extending portion 122 extending from the proximal end 124 of the hub 120. The extending portion 122 comprises a plurality of openings 126 configured for receiving the gripper 232. The openings 126 comprise a first portion 127 extending aligned with the longitudinal axis of the tightening port 230 and a second portion 129 approximately aligned perpendicularly with the longitudinal axis L. As such, upon insertion of the gripper 232 into the extending portion 122 of the hub 120, the posts 238 are received within the first portion 127 of the hub 120 and the gripper 232 may be rotated such that the posts 238 are received within the second portions 129 of the openings 126 to secure the gripper 232 with the hub 120. This secures the gripper 232 onto the hub 120 (FIG. 1) and over the medical device, for example the catheter 170, inserted through the hub 120 and the introducer sheath 100 (FIG. 1). After insertion of the gripper 232, the base 250 may be engaged with the gripper 232, as will be described further with reference to FIGS. 6A-6B.

Figures 6A, 6B:
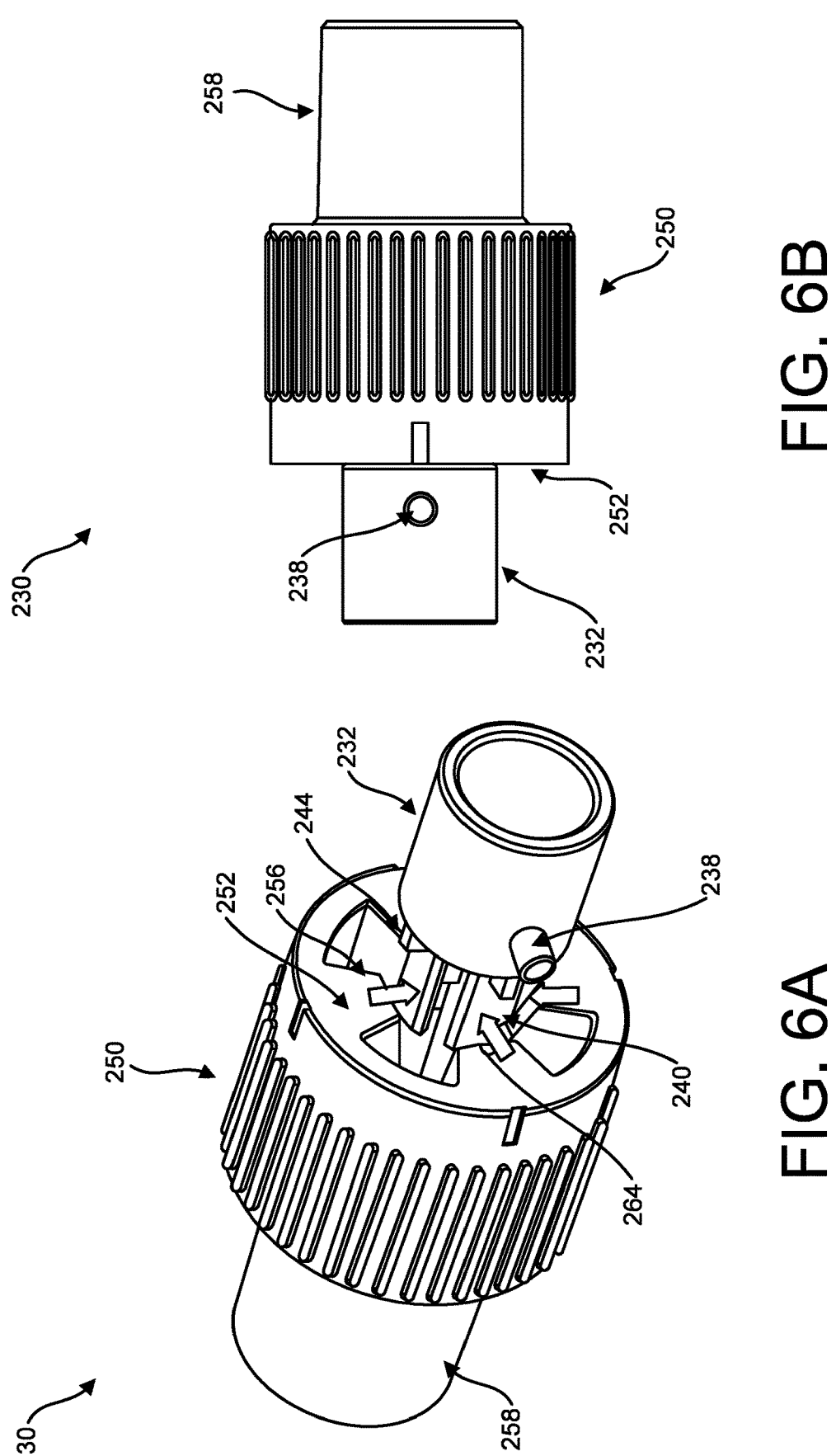
FIG. 6A illustrates a perspective view of a gripper and a base of a tightening port prior to engagement, in accordance with embodiments of the present disclosure.
FIG. 6B illustrates a perspective view of the gripper and the base of FIG. 6A after engagement, in accordance with embodiments of the present disclosure.

FIG. 6A illustrates the base 250 just prior to engagement with the gripper 232. Prior to the engagement of the base 250 and the gripper 232, the base 250 and the gripper 232 are positioned over the catheter 170 and/or the medical device extending through the base 250 and the gripper 232 and into the hub 120 (FIG. 1), however the gripper 232 is not completely radially and axially secured over the catheter 170. As such, in this configuration, the operator is able to move or reposition the catheter 170 as necessary for described positioning within the introducer sheath 100, the blood vessel V (FIG. 1), or other portion of the patient's vasculature. When the base 250 is positioned onto the gripper 232, the plurality of protrusions 240 of the gripper 232 are configured for reception by the base 250. As disclosed above, the plurality of protrusions 240 each comprise the block 244 extending from each of the plurality of protrusions 240. Further, as illustrated, each of the plurality of engagement features 256 of the base 250 includes a detent 264 positioned within the engagement features 256. The detents 264 are sized and configured for receiving the blocks 244 of each of the plurality of protrusions 240 of the gripper 232. The engagement between the plurality of engagement features 256 and the plurality of protrusions 240 of the gripper 232 push the protrusions 240 of the gripper 232 radially inward onto the catheter 170, or other medical device, that extends within the gripper 232. In other words, when the plurality of protrusions 240 engage with the engagement features 256, the plurality of protrusions 240 are forced radially inward to compress onto the catheter 170 to axially secure the catheter 170 within the tightening port 230. Additionally, the engagement of the blocks 244 and the detents 264 ensures radial securement of the gripper 232 and the base 250 so that the gripper 232 does not twist or rotate relative to the base 250. In this way, the base 250 securely engages with the gripper 232 so that the gripper 232 constricts the movement of the catheter 170.

Figure 7B:
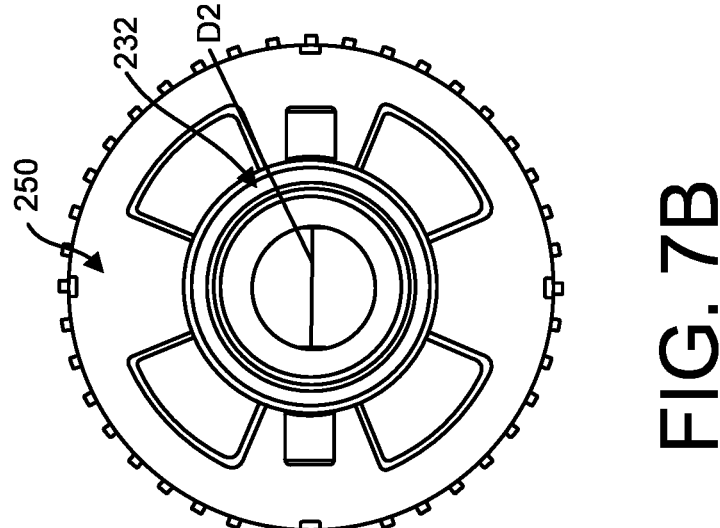
FIG. 7B illustrates a cross sectional view of a gripper and a base of a tightening port, in accordance with embodiments of the present disclosure.
Figure 7A:
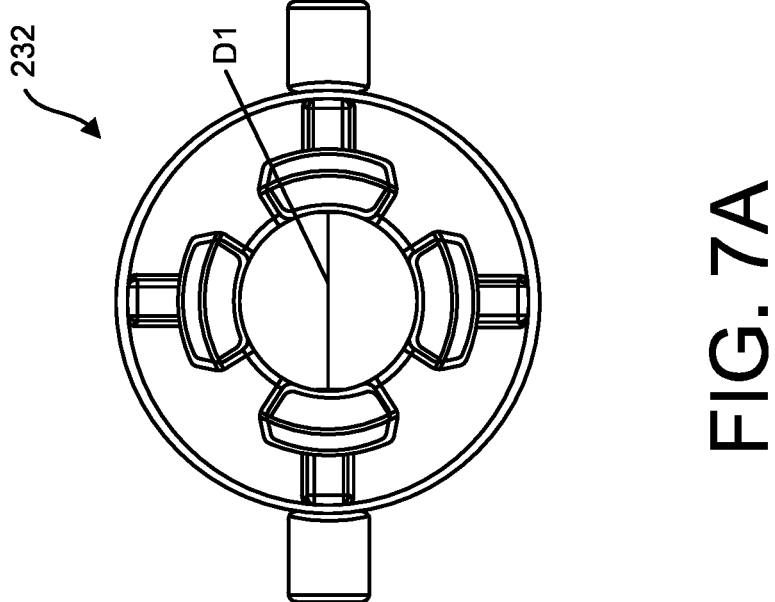
FIG. 7A illustrates a cross sectional view of a gripper of a tightening port, in accordance with embodiments of the present disclosure.

FIG. 7A illustrates the gripper 232 prior to engagement with the base 250. In this configuration, the gripper 232 has an initial inner diameter D1. In various embodiments, the initial inner diameter D1 has a value between 2 mm and 5 mm. For example, the value of the initial inner diameter D1 may be approximately 3.33 mm. FIG. 7B illustrates the gripper 232 after engagement with the base 250. In this configuration, the gripper 232 comprises a compressed inner diameter D2. The compressed inner diameter D2 may have a value of between 1.0 mm and 4.5 mm. For example, the value of the compressed inner diameter D2 may be approximately 2.8 mm. The compressed inner diameter D2 is less than the initial inner diameter D1. In this way, the gripper 232 engages with the external surface of the catheter 170 to secure the catheter 170 within the tightening port 230.

Figure 8:
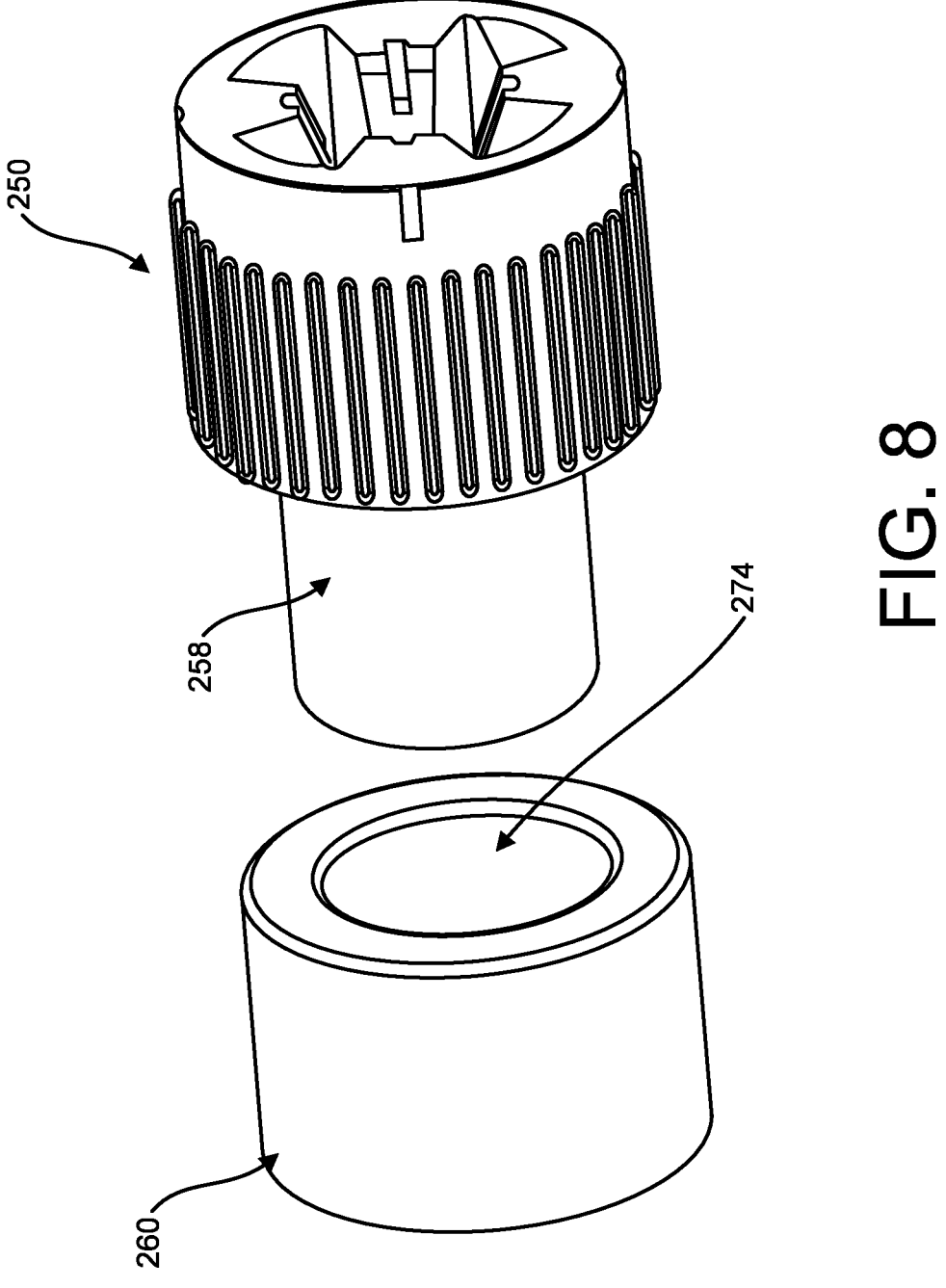
FIG. 8 is a perspective view of a base and a sleeve holder of a tightening port, in accordance with embodiments of the present disclosure.

Further, as shown in FIG. 8, the base 250 may also be engaged with the sleeve holder 260. The sleeve holder 260 has a generally cylindrical orientation such that it defines a lumen 274 that allows the sleeve holder 260 to be positioned over the base 250 (FIG. 3). The sleeve holder 260 is configured for gripping a sterile sleeve that may be positioned over the catheter 170. For example, the sterile sleeve may be positioned over the catheter 170 and the sleeve holder 260 may be positioned over the catheter sterile sleeve and engaged with the base 250 to maintain the sterile sleeve against the base 250 and position over catheter 170. In this way, the tightening port 230 may increase the ease of which the operator can securely grasp the catheter 170 and or the tightening port 230 to operate the device, while ensuring that the sterile sleeve maintains its positioning.

Figure 9:
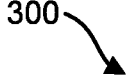
FIG. 9 illustrates a flow chart for a method of delivering at least one medical device into a blood vessel, in accordance with embodiments of the present disclosure.
Figure 9:
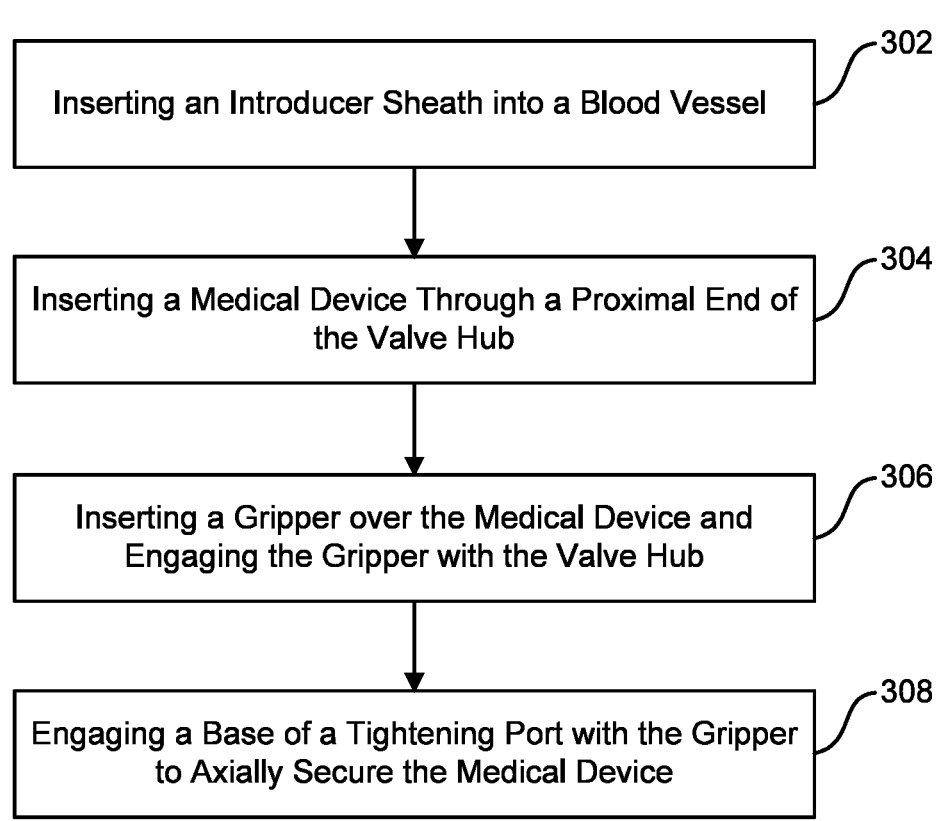

With reference to the above-described figures and FIG. 9, a method 300 for delivering at least one medical device, for example the catheter 170, into the blood vessel V will be described. At block 302, includes inserting the introducer sheath 100 into the blood vessel V. In this example, the introducer sheath 100 comprises the hub 120 positioned on the proximal end 106 of the introducer sheath 100. Further, at block 304, the method 300 includes inserting the catheter 170, or any other suitable medical device, through the proximal end 124 of the hub 120 and into the introducer sheath 100. At block 306, the method 300 further includes inserting the gripper 232 of the tightening port 230 over the catheter 170 and engaging the gripper 232 with the proximal end 124 of the hub 120. For example, this may include engaging the posts 238 with the openings 126 of the hub 120 as described with reference to FIG. 5. In this embodiment, inserting the gripper 232 of the tightening port 230 over the catheter 170 also includes inserting the base 250 and the sleeve holder 260 over the catheter 170. In various other embodiments, the tightening port 230 may be preassembled on the proximal end 106 of the introducer sheath 100 or on a medical device such as catheter 170. In other words, the gripper 232, the base 250 and the sleeve holder 260 may be positioned on the introducer sheath 100 (for example on hub 120) or towards the proximal end of the catheter 170 without being fully assembled and engaged until actuation by the operator. In other embodiments, only the gripper 232 is preassembled on the introducer sheath 100 or the hub 120. In these embodiments, the gripper 232 may be engaged with the introducer sheath 100 or the hub 120 (FIG. 1) prior to the engagement with the base 250 and the sleeve holder 260, and prior to the insertion of the catheter 170 into the hub 120.

At block 308, the method 300 further includes engaging the base 250 of the tightening port 230 with the gripper 232, such that the base 250 is positioned over the gripper 232 and the catheter 170 to axially secure the catheter 170 and to rotationally secure the gripper 232 and the base 250 of the tightening port 230. More specifically, as descried with reference to FIGS. 6A-7B, engaging the base 250 with the gripper 232 includes engaging the plurality of engagement features 256 of the base 250 with the plurality of protrusions 240 of the gripper 232 and engaging each block 244 and each detent 264. This engagement reduces the diameter of the tightening port 230 to be defined by the compressed inner diameter D2 of the gripper 232 rather than the initial inner diameter D1 of the gripper 232 and rotationally secures the gripper 232 and the base 250. More specifically, the positioning of the blocks 244 within the detents 264 inhibits rotational movement of the gripper 232 relative to the base 250. Further, the method may additionally include engaging the sleeve holder 260 with the base 250 to grip and secure the positioning of a sterile sleeve over the catheter 170.

While described herein as being used with the catheter 170, the introducer sheath 100, the hub 120 and the tightening port 130, 230 may be configured for use with various other medical devices. Various modifications and additions can be made to the exemplary embodiments discussed without departing from the scope of the present invention. For example, while the embodiments described above refer to particular features, the scope of this invention also includes embodiments having different combinations of features and embodiments that do not include all of the above-described features.

The invention claimed is:

1. A tightening port for use with a hemostasis valve hub of a sheath, the tightening port comprising:
   a gripper configured for engagement with the hemostasis valve hub, the gripper having a proximal end, a distal end, a cylindrical body defining a lumen, and a plurality of protrusions extending from the proximal end; and
   a base having a cylindrical body and a lumen defined therethrough for receiving a portion of the gripper, and the base has a plurality of engagement features configured for engaging with the plurality of protrusions of the gripper;
   wherein the lumen of the gripper has an initial diameter prior to engagement with the base, and the lumen of the gripper has a compressed diameter after engagement with the base, wherein the compressed diameter is less than the initial diameter,
   wherein the gripper comprises one or more posts configured for engaging with the hemostasis valve hub; and
   wherein the plurality of engagement features comprises at least four protrusions that extend radially inward from an outer circumference of the base.

2. The tightening port of claim 1, wherein the one or more posts comprises a plurality of posts configured for engaging with the hemostasis valve hub.

3. The tightening port of claim 1, wherein the plurality of protrusions of the gripper comprises at least four protrusions extending from the cylindrical body.

4. The tightening port of claim 1, wherein the base has an outer surface with a plurality of ribs extending circumferentially around the outer surface.

5. The tightening port of claim 1, wherein each of the protrusions comprises a detent configured for receiving a portion of the protrusions of the gripper for engagement with the gripper.

6. The tightening port of claim 1, wherein the initial diameter has a value of approximately 3.3 mm.

7. The tightening port of claim 1, wherein the compressed diameter has a value of approximately 2.8 mm.

8. The tightening port of claim 1, wherein the base comprises an extension configured for receiving a sleeve holder.

9. A tightening port for use with a hemostasis valve hub of a sheath, the tightening port comprising:
   a gripper configured for engagement with the hemostasis valve hub, the gripper having a proximal end, a distal end, a cylindrical body defining a lumen, and a plurality of protrusions extending from the proximal end, wherein the plurality of protrusions of the gripper comprises at least four protrusions extending from the cylindrical body; and
   a base having a cylindrical body and a lumen defined therethrough for receiving a portion of the gripper, and the base has a plurality of engagement features configured for engaging with the plurality of protrusions of the gripper;
   wherein the lumen of the gripper has an initial diameter prior to engagement with the base, and the lumen of the gripper has a compressed diameter after engagement with the base, wherein the compressed diameter is less than the initial diameter,
   wherein the gripper comprises one or more posts configured for engaging with the hemostasis valve hub; and
   wherein each of the protrusions of the gripper has a block extending radially outward from the protrusion.

10. A delivery system for introducing at least one medical device into a blood vessel, the delivery system comprising:
   a sheath configured for insertion into the blood vessel, the sheath having a proximal end and a distal end;
   a hemostasis valve hub having a proximal end and a distal end and the distal end configured for attachment with the proximal end of the sheath; and a tightening port configured for attachment with the proximal end of the hemostasis valve hub, the tightening port comprising:

a gripper configured for engagement with the hemostasis valve, the gripper having a proximal end, a distal end, a cylindrical body defining a lumen, and a plurality of protrusions extending from the proximal end; and a base having a cylindrical body and a lumen defined therethrough for receiving a portion of the gripper, and the base has a plurality of engagement features configured for engaging with the plurality of protrusions of the gripper; and wherein the lumen of the gripper has an initial diameter prior to engagement with the base, and the lumen of the gripper has a compressed diameter after engagement with the base, wherein the compressed diameter is less than the initial diameter;

wherein the gripper comprises a plurality of posts configured for engaging with the hemostasis valve hub; and wherein the plurality of engagement features of the base comprises a plurality of protrusions extending radially inwardly from an outer circumference of the base.

11. The delivery system of claim 10, wherein the tightening port further comprises the base having an extension and a sleeve holder engaged with the extension of the base.

12. The delivery system of claim 10, wherein each of the plurality of engagement features comprises a detent for receiving a portion of the each of the plurality of protrusions of the gripper.

13. The delivery system of claim 10, wherein each of the plurality of protrusions includes a block extending radially outward from the protrusion and is received within each of the detents of the base.

* * * * *